United States Patent
Greaves et al.

(10) Patent No.: US 7,182,790 B2
(45) Date of Patent: Feb. 27, 2007

(54) USE OF AT LEAST ONE NINHYDRIN DERIVATIVE FOR DYEING

(75) Inventors: Andrew Greaves, Montrevain (FR); Grégory Plos, Tokyo (JP)

(73) Assignee: L'Oreal S.A., Paris (FR)

( * ) Notice: Subject to any disclaimer, the term of this patent is extended or adjusted under 35 U.S.C. 154(b) by 392 days.

(21) Appl. No.: 10/898,245

(22) Filed: Jul. 26, 2004

(65) Prior Publication Data

US 2005/0050651 A1 Mar. 10, 2005

Related U.S. Application Data

(60) Provisional application No. 60/499,392, filed on Sep. 3, 2003.

(30) Foreign Application Priority Data

Jul. 25, 2003 (FR) .................................. 03 09175
Mar. 4, 2004 (FR) .................................. 04 02242

(51) Int. Cl.
*A61K 7/13* (2006.01)

(52) U.S. Cl. ........................ 8/405; 8/406; 8/407; 8/410; 8/411; 8/421; 8/437; 8/607; 568/327

(58) Field of Classification Search .................... 8/405, 8/406, 407, 410, 411, 421, 437, 607; 568/327
See application file for complete search history.

(56) References Cited

FOREIGN PATENT DOCUMENTS

| DE | 43 17 855 A | 12/1994 |
|---|---|---|
| DE | 4317855 A1 * | 12/1994 |
| DE | 19717222 A1 | 10/1998 |
| DE | 19745355 A1 | 4/1999 |
| DE | 19845481 A1 | 4/2000 |

OTHER PUBLICATIONS

English Abstract of the Patent No. DE 4317855 A1.*
STIC Search Report (Aug. 4, 2006).*
Database WPI, Derwent Publications Ltd., London, GB; AN 1973-22659U, XP002285499.
English language Derwent Abstract of DE 43 17 855 A, Dec. 1, 1994.
D. Hauze et al., "New Reagents for the Development of Fingerprints" Almog, Springe, ed., *Proceedings of the International Symposium of Fingerprint Detection and Identification*, Ne'urim, Israel, 1995, 119-123.
R. Hark et al., "Novel Approaches Toward Ninhydrin Analogs", *Tetrahedron Lett.* 1994, 35, 7719-7722.
R. Gleiter et al., "1,2,3,5,6,7-s-Hydrindacenehexone and 1,2,3,6,7,8-Pyrenehexone-Two New Strong Acceptors," *Ang. Chem.*, Int. Ed. Eng. 1980, 19, 715-716.
English Language Derwent Abstract of DE 19845481 A1.
English Language Derwent Abstract of DE 19745355 A1.
English Language Derwent Abstract of DE 19717222 A1.

* cited by examiner

*Primary Examiner*—Eisa Elhilo
(74) *Attorney, Agent, or Firm*—Finnegan, Henderson, Farabow, Garrett & Dunner, L.L.P.

(57) ABSTRACT

A composition comprising, in a medium that is suitable for dyeing, at least one ninhydrin derivative chosen from compounds of formula (I) and tautomers thereof:

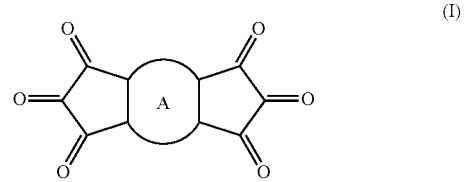

wherein:

A represents a fused or non-fused, at least 6-membered aromatic mono- or polycyclic group, possibly comprising at least one hetero atom chosen from nitrogen, oxygen, sulphur, and phosphorus atoms, a dyeing process using the composition, and a multi-component coloring agent comprising the composition.

26 Claims, No Drawings

USE OF AT LEAST ONE NINHYDRIN DERIVATIVE FOR DYEING

This application claims benefit of U.S. Provisional Application No. 60/499,392, filed Sep. 3, 2003.

The present disclosure relates to compositions for dyeing a keratin material, for example, hair dye compositions comprising at least one ninhydrin derivative, and, optionally combined with a compound containing a primary or secondary amine function or a compound containing an activated methylene function, to a dyeing process using such compositions and to a multi-component coloring agent for performing such a process.

It is common, and has been for many years, for people to wish to modify the color of their skin, their eyelashes or their hair, for example to mask their grey hair. Several techniques have been developed to do this.

It is known practice to dye human keratin fibers, such as the hair, with dye compositions containing oxidation dye precursors, which are generally known as oxidation bases. These oxidation bases are colorless or weakly colored compounds which, when combined with oxidizing products, give rise to colored compounds by a process of oxidative condensation. These dyes are insoluble and are trapped inside the hair fiber.

It is also known that the shades obtained with these oxidation bases can be varied by combining them with couplers or coloration modifiers. The variety of molecules used as oxidation bases and couplers allows a wide range of colors to be obtained.

The colorations obtained may show good shampoo-fastness. However, the oxidation reaction takes place using oxidizing products such as aqueous hydrogen peroxide solution in basic medium. These oxidizing agents may attack the keratin of the hair, the cosmetic and mechanical properties of which may become greatly degraded in the case of repeated colorations.

It is also known practice to dye human keratin fibers by direct dyeing, which comprises applying to the keratin fibers direct dyes, which are colored and coloring molecules that have affinity for the fibers. Examples of direct dyes conventionally used that may be mentioned include nitro dyes, benzene dyes, anthraquinone dyes, nitropyridine dyes, azo dyes, cationic azo dyes, xanthene dyes, acridine dyes, azine dyes, triaryl-methane dyes or natural dyes.

Although the colorations thus obtained are certainly very chromatic and may not cause any chemical degradation of keratin, they have the drawback of being only temporary or semi-permanent, i.e., they may fade out after only 4 to 5 shampoo washes.

There is consequently still a desire for dyeing systems and processes that can give fast results without involving the use of oxidizing agents that may degrade the keratin materials.

The present inventors have discovered, that the use of ninhydrin derivatives described in greater detail hereinbelow may makes it possible to dye keratin fibres, such as hair, with fastness equivalent to or greater than that obtained by oxidation dyeing, and in the absence of strong oxidizing agents, thus making it possible to keep the keratin materials from degrading.

In one embodiment, the at least one ninhydrin derivative mentioned above may, for example, be used in combination with compounds comprising at least one labile hydrogen, such as compounds comprising at least one group chosen from primary and secondary amine groups and compounds comprising at least one activated methylene functional group.

The colorations thus obtained may show good chromaticities and may be distinguished by excellent wash-fastness (several tens of shampoo washes).

Disclosed herein is a composition comprising, in a medium that is suitable for dyeing, at least one ninhydrin derivative chosen from compounds of formula (I) and tautomers thereof:

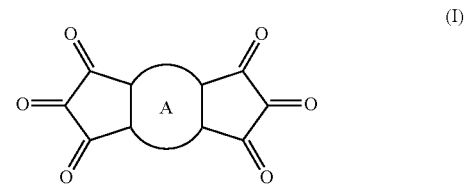

wherein:

A represents a fused or non-fused, at least 6-membered aromatic mono- or polycyclic group possibly comprising at least one hetero atom chosen from nitrogen, oxygen, sulphur and phosphorus.

The group A may, for example, be chosen from phenyl, biphenyl, naphthalenyl, anthracenyl, pyridyl, quinolyl, indolyl, indolizinyl, quinolizinyl, carbazolyl, pyranyl, xanthenyl, and thiophenyl groups. In one embodiment, the group A may, for example, be chosen from phenyl and thiophenyl groups.

The group A may be substituted with at least one group chosen from halo groups, such as chloro, iodo, bromo and fluoro; $C_1$–$C_6$ alkyl groups; hydroxyl groups; $C_1$–$C_6$ alkoxy groups; amino groups; mono- and di($C_1$–$C_6$ alkyl)amino groups; mono- and dihydroxy($C_1$–$C_6$ alkyl)amino groups; tri($C_1$–$C_6$ alkyl)ammonio groups; imidazolyl groups; pyridyl groups; thio groups; ($C_1$–$C_6$ alkyl)thio groups; thio ($C_1$–$C_6$ alkyl)groups; ($C_1$–$C_6$ alkyl)carbonyl groups; hydrogenocarbonyl groups; hydroxycarbonyl groups; ($C_1$–$C_6$ alkoxy)carbonyl groups; nitro groups and sulphonato groups; and corresponding protonated groups, such as ammonio, imidazolio and pyridinio.

Such compositions may, for example, be useful for dyeing keratin fibres, such as hair.

In one embodiment, A is chosen so as to form by condensation with the two $C_5$-trione rings a system comprising delocalized π electrons.

The at least one ninhydrin derivative of formula (I) above may be used in a cosmetically acceptable medium comprising, for example, a large fraction of water. When the at least one ninhydrin derivative of formula (I) is dissolved in such an aqueous medium, the at least one ninhydrin derivative of formula (I) is in hydration equilibrium with the gem-diol (or carbonyl hydrate) form corresponding to formula (Ia) below:

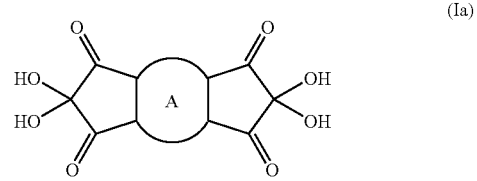

In one embodiment, the at least one ninhydrin derivative of formula (I) may be chosen from compounds of formula (I) but also the corresponding hydrated forms of formula (Ia).

Examples of the at least one ninhydrin derivative that may be used for dyeing keratin fibres include:

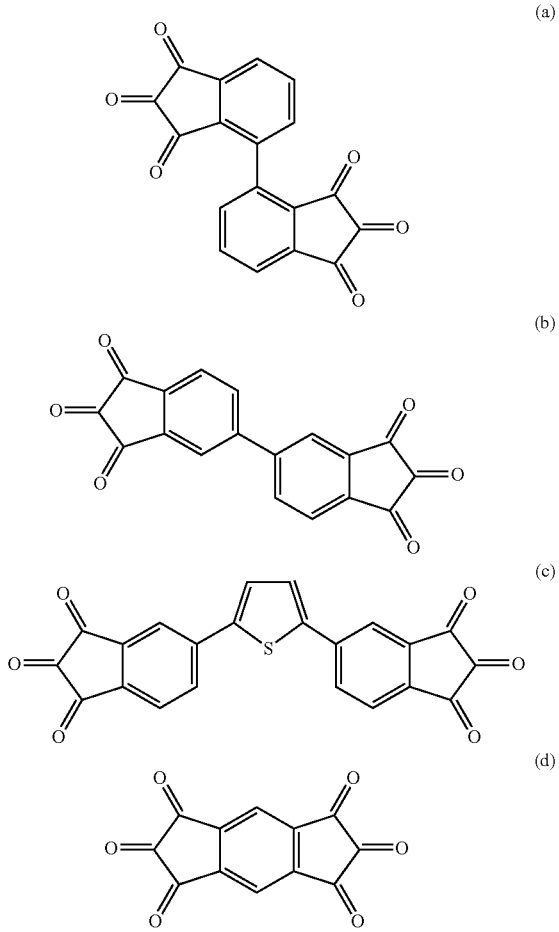

The at least one ninhydrin derivative disclosed herein is known by those skilled in the art. The synthesis of the above at least one ninhydrin derivative is described in the following publications:
(a) Hauze D. B., Petrovskaia O., Joulliée M. M., Hark R. R., "New Reagents for the Development of Fingerprints" in Almog J., Springer E., ed. Proceedings of the International Symposium on Fingerprint Detection and Identification, Ne'urim, Israel: Hemed Press, 1995, 119–123;
(b) Hark R. R., Hauze D. B., Petrovskaïa O., Joullié M. M., Jahouari R., McComiskey P., "Novel Approaches Toward Ninhydrin Analogs", Tetrahedron Lett. 1994, 35, 7719–7722; and
(c) Gleiter R., Schang P., "1,2,3,5,6,7-s-Hydrindacenehexone and 1,2,3,6,7,8-Pyrenehexone-Two New Strong Acceptors," Ang. Chem., Int. Ed. Eng. 1980, 19, 715–716

In accordance with the present disclosure, the ninhydrin compounds of formula (I) described above may be used alone for dyeing keratin materials. The reason for this is that these compounds are capable of generating colored molecules with the amine functions of keratin (colored reaction).

The compounds of formula (I) may also be used in combination with at least one activator, which makes it possible to modify the reaction kinetics of the ninhydrin compound with the keratin material. In one embodiment, the at least one activator may be chosen from oxidizing agents; reducing agents; Brönsted acids; metal catalysts, such as catalysts based on a transition metal, such as iron, platinum, and palladium; proteins, such as enzymes; compounds that modify the ionic strength of the medium, such as NaCl salts; and compounds comprising at least one labile hydrogen, such as compounds comprising at least one group chosen from primary and secondary amine functional groups and compounds comprising at least one activated methylene functional group.

In one embodiment, the compounds comprising at least one group chosen from primary amine and secondary amine functional groups may, for example, be chosen from aromatic amines.

Examples of the aromatic amines include N,N-dimethyl-p-phenylenediamine, N,N-diethyl-p-phenylenediamine, N-(2-hydroxyethyl-N-ethyl-p-phenylenediamine, N,N,-bis(2-hydroxyethyl-p-phenylenediamine, N-(2-methoxyethyl-p-phenylenediamine, 2,3-, 2,4- or 2,5-dichloro-p-phenylenediamine, 2-chlorophenylenediamine, 2,5-dihydroxy-4-morpholinoaniline dihydrobromide, 2-, 3- or 4-aminophenol, 2-aminomethyl-4-aminophenol, 2-hydroxymethyl-4-aminophenol, ortho-phenylenediamine, p-phenylenediamine, ortho-toluenediamine, 2,5-diaminotoluene, 2,5-diaminophenol, 2,5-diaminophenethol, 4-amino-3-methylphenol, 2-(2,5-diaminophenyl)ethanol, 2,4-diaminophenoxyethanol, 2-(2,5-diaminophenoxy)ethanol, 4-methyl-aminoaniline, 3-amino-4-(2'-hydroxyethyloxy)aniline, 3,4-methylenediaminoaniline, 3,4-methylenedioxyaniline, 3-amino-2,4-dichlorophenol, 4-methylaminophenol, 2-methyl-5-aminophenol, 3-methyl-4-aminophenol, 2-methyl-5-(2-hydroxyethylamino)phenol, 6-methyl-3-amino-2-chlorophenol, 2-methyl-5-amino-4-chlorophenol, 3,4-methylenedioxyphenol, 5-(2-hydroxyethylamino)$_4$-methoxy-2-methylphenol, 4-amino-2-hydroxymethylphenol, 1,3-diamino-2,4-dimethoxybenzene, 2-, 3- and 4-aminobenzoic acid, 2-amino-, 3-amino- and 4-aminophenylacetic acid, 2,3-, 2,4-, 2,5-, 3,4- and 3,5-diaminobenzoic acid, 4-amino- and 5-aminosalicylic acid, 3-amino-4-hydroxybenzoic acid, 4-amino-3-hydroxybenzoic acid, 2-amino, 3-amino- or 4-aminobenzenesulphonic acid, 3-amino-4-hydroxybenzenesulphonic acid, 4-amino-3-hydroxynaphthalene-1-sulphonic acid, 6-amino-7-hydroxynaphthalene-2-sulphonic acid, 7-amino-4-hydroxynaphthalene-2-sulphonic acid, 4-amino-5-hydroxynaphthalene-2, 7-di-sulphonic acid, 3-amino-2-naphthoic acid, 3-aminophthalic acid, 5-aminoisophthalic acid, 1,3,5-triaminobenzene, 1,2,4-triaminobenzene, 1,2,4,5-tetraminobenzene, 2,4,5-triaminophenol, pentaminobenzene, hexaminobenzene, 2,4,6-triaminoresorcinol, 4,5-diaminopyrocatechol, 4,6-diaminopyrogallol, 3,5-diamino-4-hydroxypyrocatechol, and aromatic anilines and aromatic phenols comprising at least one aromatic functional group, corresponding to formula (II)

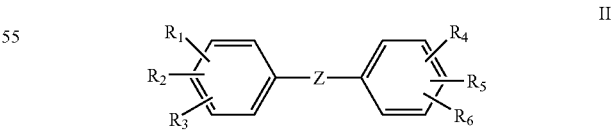

wherein:

$R_1$ is chosen from hydroxyl and amino groups optionally substituted with at least one group chosen from $C_{1-4}$ alkyl, $C_{1-4}$ hydroxyalkyl, and $(C_{1-4}$ alkoxy$)(C_{1-4}$ alkyl$)$ groups;

$R_2$, $R_3$, $R_4$, $R_5$ and $R_6$, which may be identical or different, are each independently chosen from a hydrogen atom, a hydroxyl group, and an amino group, optionally substituted with at least one group chosen from $C_{1-4}$ alkyl, $C_{1-4}$ hydroxyalkyl,($C_{1-4}$ alkoxy)($C_{1-4}$ alkyl), carboxylic acid, and sulphonic acid groups;

Z is chosen from a direct bond, saturated and unsaturated, optionally hydroxylated $C_{1-4}$ hydrocarbon-based chains, a group chosen from carbonyl, sulphonyl, and imino groups, an atom chosen from oxygen and sulphur atoms, and groups of formula Q-($CH_2$—P—$CH_2$-Q')$_o$ wherein P is chosen from a direct bond, —$CH_2$—, and —CHOH— groups, Q and Q', which may be identical or different, are each independently chosen from an oxygen atom, groups $NR_7$, wherein $R_7$ is chosen from a hydrogen atom, $C_{1-4}$ alkyl and $C_{1-4}$ hydroxyalkyl groups, and groups O—($CH_2$)$_p$NH and NH—($CH_2$)$_{p'}$—O wherein p and p', which may be identical or different, are equal to 2 or 3 and o is a number ranging from 1 to 4.

In one embodiment, the non-aromatic primary and secondary amines are, for example, chosen from 2-aminoethanol, 2-methoxyethylamine, 2-ethoxyethylamine, 2-(2-aminoethoxy)ethanol, 2- and 3-aminopropanol, 2,3-dihydroxypropylamine, 4-hydroxypropyl-amine, 2-aminopropane-1,3-diol, 2-amino-2-methylpropanol, 2-amino-2-methylpropane-1,3-diol, 2-amino-2-hydroxymethylpropane-1,3-diol, tetrahydropentylamine, pentahydroxyhexylamines, such as glucamine, D-glucosamine, D-galactosamine, 1,2-diaminoethane, 1,2- and 1,3-diaminopropane, 1,3-diamino-2-propanol, 2-(2-aminoethyl-amino) ethylamine, 2-(2-aminoethylamino)ethanol, 3-(2-aminoethylamino)propylamine, and 3-(2-aminoethylamino) propanol.

The compounds comprising an activated methylene functional group may be chosen, for example, from the following: 1,2,3,3-tetramethyl-3H-indolium iodide, 1,2,3,3-tetramethyl-3H-indolium p-toluenesulphonate, 1,2,3,3-tetramethyl-3H-indolium methanesulphonate, 1,3,3-trimethyl-2-methyleneindoline, 2,3-dimethylbenzothiazolium iodide, 2,3-dimethylbenzothiazolium p-toluenesulphonate, rhodanine, rhodanine-3-acetic acid, 1-ethyl-2-quinaldinium iodide, 1-methyl-2-quinaldinium iodide, barbituric acid, thiobarbituric acid, 1,3-dimethylthiobarbituric acid, diethylthiobarbituric acid, oxindole, 3-indoxy acetate, coumarone, and 1-methyl-3-phenyl-2-pyrazolinone.

The compounds comprising at least one group chosen from primary and secondary amine groups and compounds comprising at least one activated methylene functional group, and also other compounds comprising at least one labile hydrogen, are described in Patent Application Nos. DE 43 17 855, DE 197 17 222, DE 198 45 481, and DE 197 45 355, wherein these compounds may be used for dyeing keratin fibres in combination with compounds other than the at least one ninhydrin derivative of formula (I).

When the at least one ninhydrin derivative of formula (I) is used in combination with at least one compound chosen from compounds comprising at least one group chosen from primary and secondary amines and compounds comprising at least one activated methylene functional group, it may be necessary for these various reagents to be stored separately in order to avoid a premature colored reaction. The reagents are thus placed in contact only immediately before application to the hair, by extemporaneous mixing of two compositions comprising, respectively, the at least one ninhydrin derivative and the at least one compound comprising at least one labile hydrogen, for example, the compounds comprising at least one group chosen from primary and secondary amines and compounds comprising at least one activated methylene functional group. The reagents may also be placed in contact directly on the hair by successive application of the various reagents.

Further disclosed herein is a multi-component coloring agent comprising,
  at least one first component comprising, at least one composition (a) comprising at least one ninhydrin derivative of formula (I), and
  at least one second component comprising at least one composition (b) comprising at least one activator which makes it possible to modify the reaction kinetics of the at least one ninhydrin compound with a keratin material.

In one embodiment, the multi-component coloring agent may be in the form of a multi-compartment kit comprising at least one first compartment comprising the at least one first component (composition (a)) and at least one second compartment comprising the at least one second component (composition (b)).

Also disclosed herein is a cosmetic dye composition comprising at least one ninhydrin derivative of formula (I) and at least one cosmetic agent.

The at least one cosmetic agent may be chosen, for example, from vitamins; saccharides; oligosaccharides; hydrolyzed and non-hydrolyzed, modified and unmodified polysaccharides; amino acids; oligopeptides; peptides; hydrolyzed and non-hydrolyzed, modified and unmodified proteins; polyamino acids; enzymes; branched and unbranched fatty acids and fatty alcohols; animal, plant, and mineral waxes; ceramides and pseudoceramides; hydroxylated organic acids; UV-screening agents; antioxidants; free-radical scavengers; chelating agents; antidandruff agents; seborrhoea regulators; calmatives; cationic, anionic, nonionic and amphoteric surfactants; cationic, anionic, neutral, and amphoteric polymers; organomodified and non-organomodified silicones; mineral, plant, and animal oils; polyisobutenes; poly($\alpha$-olefins); fatty esters, anionic polymers in dissolved and dispersed form; nonionic polymers in dissolved and dispersed form; reducing agents; solvents; hair dyes, such as direct dyes and oxidation dye precursors (bases and/or couplers) other than the compounds comprising at least one functional group chosen from primary and secondary amine functional groups; oxidizing agents, such as hydrogen peroxide optionally combined with persalts; and pigments.

The at least one cosmetic agent may be present in an amount ranging from 0.001% to 50% by weight, for example, from 0.01% to 20% by weight and, further, for example, from 0.1% to 10% by weight, relative to the total weight of the cosmetic composition.

In one embodiment, the dye composition disclosed herein comprises at least one cosmetic agent chosen from surfactants and polymers, wherein these agents may be nonionic, cationic, anionic or amphoteric in nature.

The dye compositions disclosed above are generally stable on storage when they contain, as sole reagents, ninhydrin compounds of formula (I). However, when they contain both ninhydrin compounds of formula (I) and compounds containing labile hydrogen such as primary or secondary amines or compounds containing an activated methylene function, these compositions should be used immediately after mixing the at least one ninhydrin compound of formula (I) with the compound(s) containing labile hydrogen.

These ready-to-use dye compositions, whether they are stable on storage or prepared immediately before use, may have a pH ranging from 2 to 12 and, for example, from 3 to 11.

The at least one ninhydrin derivative of formula (I) may be present in an amount ranging from 0.0001% to 30% by weight, relative to the total weight of the composition.

The compounds comprising at least one labile hydrogen may be present in an amount ranging from 0.0001% to 30% by weight, relative to the total weight of the composition.

A subject of the present disclosure is also a hair dyeing process comprising the application to the hair of a ready-to-use hair dye composition as described above. This composition is left in contact with the hair fibers for a time that is sufficient to obtain the desired coloration. This leave-in time is generally from 5 minutes to 1 hour, for example, from 15 to 30 minutes. The color reaction between the at least one ninhydrin compound and the amine functions of the keratin or the compounds containing labile hydrogen that are optionally present may be accelerated by heating the hair impregnated with the dye composition. The heating temperature may go up to 80° C., for example, be less than or equal to 60° C.

In one embodiment, after obtaining the desired hair coloration, the hair may be rinsed and washed.

When compounds comprising at least one labile hydrogen, such as compounds comprising at least one group chosen from primary and secondary amines or compounds comprising at least one activated methylene functional group may be used, the application of the compositions participating in the color reaction may also take place in two stages, for example, two different compositions comprising, respectively, the at least one ninhydrin derivative of formula (I) and at least one compound chosen from compounds comprising at least one group chosen from primary and secondary amines and compounds comprising at least one activated methylene functional group may be applied successively.

Further disclosed herein is a two-stage dyeing process comprising applying to the hair one after the other, in any order, at least one composition (a) and at least one composition (b) as defined above for the multi-component coloring agent.

This separate application of two reactive compositions may have the advantage of avoiding the handling of colored compositions and thus may reduce the risks of soiling materials, such as clothing.

The present inventor has found that satisfactory hair colorations may also be obtained when an intermediate rinsing step is inserted between the application of the at least one composition (a) and the application of the at least one composition (b).

Analogously with that described above, in one embodiment, the hair impregnated with composition (a) and/or (b) may be heated, for example, up to a temperature of less than or equal to 80° C., and, for example, to a temperature less than or equal to 60° C., such heating may make it possible to accelerate the color reaction and to shorten the leave-in time.

EXAMPLES

The present inventors have produced the following composition in accordance with this disclosure:

| | |
|---|---|
| 5-[5'-(2,2-dihydroxy-1,3-dioxoindan-5-yl)thiophen-2-yl]-2,2-dihydroxyindane-1,3-dione (=hydrate of the compound of formula (c)) | $10^{-2}$ mol % |
| Ethanol | 50% |
| NaOH | qs pH 7 |
| Distilled water | qs 100% |

This composition was applied to two locks of natural hair, permed, and containing 90% white hairs, each lock weighing 1 g. The bath ratio was 5, the leave-in time was 30 minutes and the temperature was 60° C. At the end of the leave-in time, the locks were rinsed and then washed with a standard shampoo.

The intensity of dyeing was evaluated by colorimetry in accordance with the CIELAB system using a CM3600d calorimeter from Minolta (illuminant D65, observation angle 10°, specular component included).

The CIELAB notation system defines a calorimetric space within which each color is defined by three parameters (L*, a* and b*):

- the parameter L* reflects the lightness of the color, the value of L* being equal to 0 for black and equal to 1 for absolute white. The higher the value of L*, the less intense the dyeing.
- the parameter a* corresponds to the axis of the mutually antagonistic green-red pairing and the parameter b* to the axis of the mutually antagonistic blue-yellow pairing.

The table below shows the L*, a* and b* parameters of the locks of natural hair and of permed hair before and after the increase in color, and also ΔE, which is defined by the following equation:

$$\Delta E = \sqrt{(L^*_{final} - L^*_{initial})^2 + (a^*_{final} - a^*_{initial})^2 + (b^*_{final} - b^*_{initial})^2}$$

ΔE reflects the overall change in color. The greater the variation in color, the greater the value of ΔE.

| Hair | | L* | a* | b* | ΔE | Color |
|---|---|---|---|---|---|---|
| natural | before dyeing | 62.80 | −0.10 | 9.52 | — | — |
| natural | after dyeing | 28.62 | −6.58 | 4.93 | 38.84 | matt |
| permed | before dyeing | 62.58 | −0.28 | 13.46 | — | — |
| permed | after dyeing | 24.88 | −2.22 | −1.35 | 43.08 | black |

What is claimed is:

1. A process for dyeing keratin material comprising:
applying to the keratin material a composition comprising, in a medium that is suitable for dyeing, at least one ninhydrin compound chosen from compounds of formula (I) and tautomers thereof:

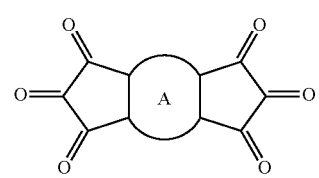

(I)

wherein:
A represents a fused or non-fused, at least 6-membered aromatic mono- or polycyclic group, possibly comprising at least one hetero atom chosen from nitrogen, oxygen, sulphur, and phosphorus atoms.

2. The process according to claim 1, wherein A is chosen from phenyl, biphenyl, naphthalenyl, anthracenyl, pyridyl, quinolyl, indolyl, indolizinyl, quinolizinyl, carbazolyl, pyranyl, xanthenyl, and thiophenyl groups.

3. The process according to claim 1, wherein A is chosen from phenyl and thiophenyl groups.

4. The process according to claim 1, wherein A is substituted with at least one group chosen from halo groups; $C_1$–$C_6$ alkyl groups; hydroxyl groups; $C_1$–$C_6$ alkoxy groups; amino groups; imidazolyl groups; pyridyl groups; mono- and di($C_1$–$C_6$ alkyl)amino groups; mono- and dihydroxy ($C_1$–$C_6$ alkyl)amino groups; tri($C_1$–$C_6$ alkyl)ammonio groups; thio groups; ($C_1$–$C_6$ alkyl)thio groups; thio($C_1$–$C_6$ alkyl)groups; ($C_1$–$C_6$ alkyl)carbonyl groups; hydrogenocarbonyl groups; hydroxycarbonyl groups; ($C_1$–$C_6$ alkoxy)carbonyl groups; nitro groups; sulphonato groups; and corresponding protonated groups.

5. The process according to claim 4, wherein the corresponding protonated groups are chosen from ammonio, imidazolio and pyridinio.

6. The process according to claim 1, wherein the at least one ninhydrin derivative of formula (I) is chosen from the following compounds:

7. The process according to claim 1, further comprising at least one activator which makes it possible to modify the reaction kinetics of the at least one ninhydrin compound with the keratin material.

8. The process according to claim 7, wherein the at least one activator is chosen from oxidizing agents, reducing agents, Brönsted acids, metal catalysts, proteins, compounds that modify the ionic strength of the medium, compounds comprising at least one labile hydrogen chosen from compounds comprising at least one group chosen from primary and secondary amines and compounds comprising at least one activated methylene functional group.

9. The process according to claim 8, wherein the compounds comprising at least one group chosen from primary and secondary amines are chosen from:

aromatic amines chosen from N,N-dimethyl-p-phenylenediamine, N,N-diethyl-p-phenylenediamine, N-(2-hydroxyethyl)-N-ethyl-p-phenylenediamine, N,N,-bis(2-hydroxyethyl)-p-phenylenediamine, N-(2-methoxyethyl)-p-phenylenediamine, 2,3-, 2,4- and 2,5-dichloro-p-phenylenediamine, 2-chloro-p-phenylenediamine, 2,5-dihydroxy-4-morpholinoaniline dihydrobromide, 2-, 3- and 4-aminophenol, 2-aminomethyl-4-aminophenol, 2-hydroxymethyl-4-aminophenol, ortho-phenylenediamine, p-phenylenediamine, ortho-toluenediamine, 2,5-diaminotoluene, 2,5-diaminophenol, 2,5-diaminophenethol, 4-amino-3-methylphenol, 2-(2,5-diaminophenyl)ethanol, 2,4-diaminophenoxyethanol, 2-(2,5-diaminophenoxy)ethanol, 4-methylaminoaniline, 3-amino-4-(2'-hydroxyethyloxy)aniline, 3,4-methylenediaminoaniline, 3,4-methylenedioxyaniline, 3-amino-2,4-dichlorophenol, 4-methylaminophenol, 2-methyl-5-aminophenol, 3-methyl-4-aminophenol, 2-methyl-5-(2-hydroxyethylamino) phenol, 6-methyl-3-amino-2-chlorophenol, 2-methyl-5-amino-4-chlorophenol, 3,4-methylenedioxyphenol, 5-(2-hydroxyethylamino)-4-methoxy-2-methylphenol, 4-amino-2-hydroxymethylphenol, 1,3-diamino-2,4-dimethoxybenzene, 2-, 3-, and 4-aminobenzoic acid, 2-amino-, 3-amino- and 4-aminophenylacetic acid, 2,3-, 2,4-, 2,5-, 3,4- and 3,5-diaminobenzoic acid, 4-amino- and 5-aminosalicylic acid, 3-amino-4-hydroxybenzoic acid, 4-amino-3-hydroxybenzoic acid, 2-amino, 3-amino- and 4-aminobenzenesulphonic acid, 3-amino-4-hydroxybenzenesulphonic acid, 4-amino-3-hydroxynaphthalene-1-sulphonic acid, 6-amino-7-hydroxynaphthalene-2-sulphonic acid, 7-amino-4-hydroxynaphthalene-2-sulphonic acid, 4-amino-5-hydroxynaphthalene-2,7-disulphonic acid, 3-amino-2-naphthoic acid, 3-aminophthalic acid, 5-aminoisophthalic acid, 1,3,5-triaminobenzene, 1,2,4-triaminobenzene, 1,2,4,5-tetraminobenzene, 2,4,5-triaminophenol, pentaminobenzene, hexaminobenzene, 2,4,6-triaminoresorcinol, 4,5-diaminopyrocatechol, 4,6-diaminopyrogallol, 3,5-diamino-4-hydroxypyrocatechol, and aromatic anilines and aromatic phenols comprising at least one aromatic functional group, corresponding to formula (II) below

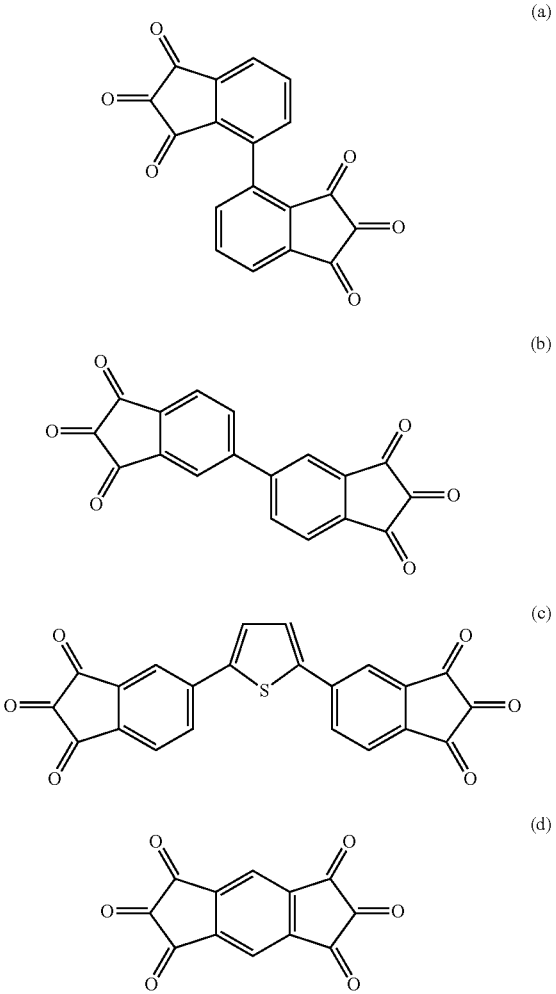

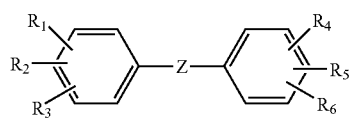

II wherein:
R₁ is chosen from hydroxyl and amino groups optionally substituted with at least one group chosen from $C_{1-4}$ alkyl, $C_4$ hydroxyalkyl, and ($C_{1-4}$alkoxy)($C_{1-4}$ alkyl) groups;
$R_2$, $R_3$, $R_4$, $R_5$ and $R_6$, which may be identical or different, are each chosen from a hydrogen atom, a hydroxyl group, and an amino group, optionally substituted with at least one group chosen from $C_{1-4}$ alkyl, $C_{1-4}$ hydroxyalkyl, ($C_{1-4}$ alkoxy)($C_{1-4}$ alkyl) groups and carboxylic and sulphonic acid groups;
Z is chosen from direct bonds, saturated and unsaturated, optionally hydroxylated $C_{1-4}$ hydrocarbon-based chains, carbonyl, sulphonyl, and imino groups, oxygen and sulphur atoms, and groups of formula Q-(CH₂—P—CH₂-Q')ₒ wherein P is chosen from a direct bond and —CH₂— and —CHOH— groups; Q and Q', which may be identical or different, are each chosen from an oxygen atom, groups NR₇, wherein R₇ is chosen from a hydrogen atom, $C_{1-4}$ alkyl and $C_{1-4}$ hydroxyalkyl groups, and groups O—(CH₂)ₚNH and NH—(CH₂)ₚ—O, wherein p and p', which may be identical or different, are equal to 2 or 3 and o is a number ranging from 1 to 4 and
non-aromatic amines chosen from 2-aminoethanol, 2-methoxyethylamine, 2-ethoxyethylamine, 2-(2-aminoethoxy)ethanol, 2- and 3-aminopropanol, 2,3-dihydroxy-propylamine, 4-hydroxypropylamine, 2-aminopropane-1,3-diol, 2-amino-2-methylpropanol, 2-amino-2-methylpropane-1,3-diol, 2-amino-2-hydroxymethylpropane-1,3-diol, tetrahydropentylamine, pentahydroxyhexylamines, glucamines, D-glucosamine, D-galactosamine, 1,2-diaminoethane, 1,2- and 1,3-diaminopropane, 1,3-diamino-2-propanol, 2-(2-aminoethylamino)ethylamine, 2-(2-aminoethylamino)ethanol, 3-(2-aminoethylamino)propylamine, and 3-(2-aminoethylamino)propanol.

10. The process according to claim 8, wherein the compounds comprising at least one activated methylene functional group are chosen from 1,2,3,3-tetramethyl-3H-indolium iodide, 1,2,3,3-tetramethyl-3H-indolium p-toluenesulphonate, 1,2,3,3-tetramethyl-3H-indolium methanesulphonate, 1,3,3-trimethyl-2-methyleneindoline, 2,3-dimethylbenzo-thiazolium iodide, 2,3-dimethylbenzothiazolium p-toluenesulphonate, rhodanine, rhodanine-3-acetic acid, 1-ethyl-2-quinaldinium iodide, 1-methyl-2-quinaldinium iodide, barbituric acid, thiobarbituric acid, 1,3-dimethylthiobarbituric acid, diethylthiobarbituric acid, oxindole, 3-indoxy acetate, coumarone, and 1-methyl-3-phenyl-2-pyrazolinone.

11. The process according to claim 1, wherein the composition has a pH ranging from 2 to 12.

12. The process according to claim 11, wherein the composition has a pH ranging from 3 to 11.

13. The process according to claim 1, wherein the at least one ninhydrin derivative of formula (I) is present in an amount ranging from 0.0001% to 30% by weight, relative to the total weight of the composition.

14. The process according to claim 8, wherein the compounds comprising at least one labile hydrogen are present in an amount ranging from 0.0001% to 30% relative to the total weight of the composition.

15. A cosmetic dye composition comprising, in a medium that is suitable for dyeing keratin fibres,
at least one ninhydrin derivative chosen from compounds of formula (I) and tautomers thereof:

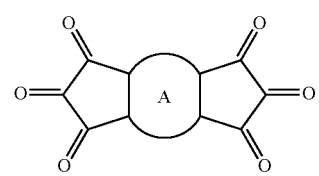

wherein:
A represents a fused or non-fused, at least 6-membered aromatic mono- or polycyclic group, possibly comprising at least one hetero atom chosen from nitrogen, oxygen, sulphur, and phosphorus atoms; and
at least one agent.

16. The composition according to claim 15, wherein the at least one agent is chosen from nonionic, cationic, anionic, and amphoteric surfactants and nonionic, cationic, anionic, and amphoteric polymers.

17. A ready-to-use cosmetic composition comprising,
at least one ninhydrin derivative chosen from compounds of formula (I) and tautomers thereof:

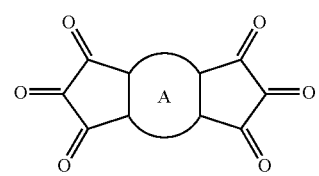

wherein:
A represents a fused or non-fused, at least 6-membered aromatic mono- or polycyclic group, possibly comprising at least one hetero atom chosen from nitrogen, oxygen, sulphur, and phosphorus atoms and
at least one compound chosen from compounds comprising at least one group chosen from primary and secondary amines and compounds comprising at least one activated methylene functional group.

18. A multi-component coloring agent comprising,
at least one first component comprising, at least one composition (a) comprising, in a medium suitable for dyeing, at least one ninhydrin derivative chosen from compounds of formula (I) and tautomers thereof:

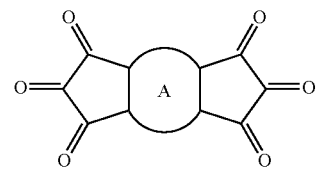

wherein:
A represents a fused or non-fused, at least 6-membered aromatic mono- or polycyclic group, possibly comprising at least one hetero atom chosen from nitrogen, oxygen, sulphur, and phosphorus atoms and
at least one second component comprising at least one composition (b) comprising at least one activator which makes it possible to modify the reaction kinetics of the at least one ninhydrin derivative of formula (I) with a keratin material.

19. The coloring agent according to claim 18, wherein the coloring agent is provided in the form of a multi-compartment kit, comprising at least one first compartment comprising the at least one composition (a) and at least one second compartment comprising the at least one composition (b).

20. A hair dyeing process comprising,
applying to hair at least one hair dye composition comprising, in a medium that is suitable for dyeing, at least one ninhydrin derivative chosen from compounds of formula (I) and tautomers thereof:

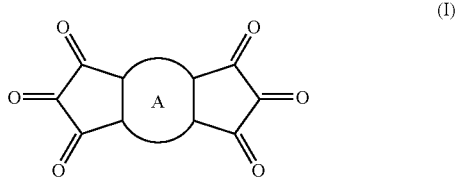

wherein:
A represents a fused or non-fused, at least 6-membered aromatic mono- or polycyclic group, possibly comprising at least one hetero atom chosen from nitrogen, oxygen, sulphur, and phosphorus atoms;
leaving the at least one hair dye composition on the hair for a leave-in time that is sufficient to obtain the desired hair coloration; and
rinsing and washing the hair.

21. The hair dyeing process according to claim 20, further comprising heating the hair impregnated with the at least one hair dye composition to a temperature of less than or equal to 80° C.

22. The hair dyeing process according to claim 21, wherein the hair impregnated with the at least one hair dye composition is heated to a temperature of less than or equal to 60° C.

23. A hair dyeing process comprising applying to the hair one after the other, in any order, at least one composition (a) comprising, in a medium suitable for dyeing, at least one ninhydrin derivative chosen from compounds of formula (I) and tautomers thereof:

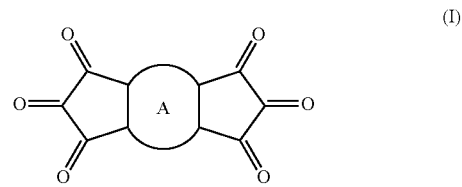

and at least one composition (b) comprising at least one activator which makes it possible to modify the reaction kinetics of the at least one ninhydrin compound with a keratin material.

24. The hair dyeing process according to claim 23, further comprising rinsing the hair after applying either the at least one composition (a) or the at least one composition (b).

25. The hair dyeing process according to claim 23, further comprising heating the hair impregnated with at least one composition (a) and/or the at least one composition (b) to a temperature of less than or equal to 80° C.

26. The hair dyeing process according to claim 25, wherein the hair impregnated with the at least one composition (a) and/or the at least one composition (b) is heated to a temperature of less than or equal to 60° C.

* * * * *

UNITED STATES PATENT AND TRADEMARK OFFICE
CERTIFICATE OF CORRECTION

PATENT NO. : 7,182,790 B2
APPLICATION NO. : 10/898245
DATED : February 27, 2007
INVENTOR(S) : Andrew Greaves et al.

It is certified that error appears in the above-identified patent and that said Letters Patent is hereby corrected as shown below:

In claim 9, column 10, line 53, "pentaminobenzene, hexaminobenzene," should read --pentaaminobenzene, hexaaminobenzene,--.

In claim 9, column 11, line 4,
"$C_4$ hydroxyalkyl," should read --$C_1$-$C_4$ hydroxyalkyl,--; and
"$(C_{1-4}$alkoxy$)(C_{1-4}$ alkyl)" should read --$(C_{1-4}$ alkoxy$)(C_{1-4}$ alkyl)--.

In claim 9, column 11, lines 21-22, "NH-$(CH_2)_p$-O" should read --NH-$(CH_2)_{p'}$-O--.

In claim 10, column 11, line 49, "3-indoxy acetate," should read --3-indoxyl acetate,--.

Signed and Sealed this

First Day of May, 2007

JON W. DUDAS
*Director of the United States Patent and Trademark Office*